United States Patent [19]

Iezzi et al.

[11] Patent Number: 5,143,886
[45] Date of Patent: Sep. 1, 1992

[54] CATALYTIC COMPOSITION FOR THE DEHYDROGENATION OF $C_2$-$C_5$ PARAFFINS

[75] Inventors: Rodolfo Iezzi; Franco Buonomo, both of San Donato Milanese; Domenico Sanfilippo, Paullo, all of Italy

[73] Assignee: Snamprogetti S.p.A., Milan, Italy

[21] Appl. No.: 650,966

[22] Filed: Feb. 5, 1991

[30] Foreign Application Priority Data

Feb. 7, 1990 [IT] Italy ........................ 19283 A/90

[51] Int. Cl.$^5$ .................. B01J 21/06; B01J 21/08; B01J 23/62
[52] U.S. Cl. ................................................. 502/242
[58] Field of Search .......................... 502/334, 242

[56] References Cited

U.S. PATENT DOCUMENTS

| | | | |
|---|---|---|---|
| 3,329,481 | 7/1967 | Young et al. | 423/333 X |
| 4,219,447 | 8/1980 | Wheelock | 502/334 X |
| 4,410,501 | 10/1983 | Taramasso et al. | 502/242 X |
| 4,413,152 | 11/1983 | Arena | 502/334 X |
| 4,666,692 | 5/1987 | Taramasso et al. | 502/242 X |
| 4,982,047 | 1/1991 | Barri et al. | 585/660 |

FOREIGN PATENT DOCUMENTS

| | | |
|---|---|---|
| 753072 | 12/1970 | Belgium . |
| 59-112836 | 6/1984 | Japan ................... 502/334 |
| 62-149338 | 7/1987 | Japan ................... 502/334 |

Primary Examiner—W. J. Shine
Assistant Examiner—Douglas J. McGinty
Attorney, Agent, or Firm—Oblon, Spivak, McClelland, Maier & Neustadt

[57] ABSTRACT

A catalytic composition for the dehydrogenation of $C_2$-$C_5$ paraffins, constituted by:
   platinum, in an amount comprised within the range of from 0.01 to 3% by weight,
   optionally tin, in an amount comprised within the range of from 0 to 1.5% by weight,
   a support selected from:
      titanated alumina,
      titanated silica and/or
      titanium silicalite
   in which the titanium amount in the same support is comprised within the range of from 0.05 to 3% by weight
is disclosed.

4 Claims, No Drawings

CATALYTIC COMPOSITION FOR THE DEHYDROGENATION OF $C_2$-$C_5$ PARAFFINS

The present invention relates to a catalytic composition for the dehydrogenation of $C_2$-$C_5$ paraffins (i.e., paraffins containing a number of carbon atoms comprised within the range of from 2 to 5 in their molecule), to obtain olefins.

The increase in demand for olefins for the production of several chemicals (such as, e.g.: high octane number gasolines, synthetic elastomers, detergents, plastics materials, ion-exchange resins, pharmaceutical products, and so forth) causes the dehydrogenation of paraffins to play a more and more considerable role from a commercial viewpoint.

Within this context, a particularly interesting process from the commercial viewpoint is the dehydrogenation of light paraffins as the source to obtain corresponding olefins for a wide range of products (such as, e.g., production of gasolines, processes of alkylation of aromatics, conversion into aromatics, isobutene production for MTBE, and so forth).

In order that this process type may find an application at the commercial level, it is necessary that paraffin conversions are high and, above all, that paraffins are selectively dehydrogenated into olefins, with any secondary reactions being minimized.

As patent literature clearly witnesses, a large number of efforts were carried out in this field and different catalytic compositions were studied.

In fact, several patents were published, which disclose the dehydrogenation of paraffins by using noble metals supported on several supports as $\gamma$-$Al_2O_3$, $SiO_2$, magnesium oxides and to which alkali metals or alkali-earth metals were added (U.S. Pat. No. 4 438 288).

The disadvantages of these systems can be found in their low activity and selectivity, and poor stability over time.

Improvements were carried out by taking into consideration other catalysts constituted by platinum, in the presence of tin (U.S. Pat. No. 3 998 900, U.S. Pat. No. 3 909 451) supported on $\gamma$-, $\eta$-, $\delta$-, $\theta$-alumina, still intended for use in paraffin dehydrogenation reactions.

However, the catalysts known from the prior art are not completely satisfactory from all viewpoints; i.e., activity performed in the process of dehydrogenation of linear paraffins, selectivity to useful reaction product and preservation of said features over time.

The present Applicant has found now that if titanium is added to the known catalyst supports used together with catalysts constituted by platinum and tin, a catalytic composition can be obtained, which shows higher selectivity and activity values in the process of dehydrogenation of paraffins to yield olefins.

The catalytic composition according to the present invention for the dehydrogenation of $C_2$-$C_5$ paraffins is characterized in that it is constituted by:
platinum, in an amount comprised within the range of from 0.01 to 3% by weight,
optionally tin, in an amount comprised within the range of from 0 to 1.5% by weight,
a support selected from:
 titanated alumina,
 titanated silica and/or
 titanium silicalite
in which the titanium amount in the same support is comprised within the range of from 0.05 to 3% by weight and is preferably comprised within the range of from 1 to 2% by weight.

Titanium-silicalite is a synthetic zeolite-type structure in whose crystal lattice silicon is partially replaced by titanium.

Said zeolite and the method to prepare it were disclosed in U.K. Pat. No. 2,071,071.

Another object of the present invention is the process for the dehydrogenation of $C_2$-$C_5$ paraffins.

Such a process is characterized in that $C_2$-$C_5$ paraffins are fed to a reactor, preferably a fluidized-bed reactor, in which the catalytic composition described above is used as the catalyst, and by preferably operating at a temperature comprised within the range of from 500° to 700° C., under a pressure comprised within the range of from 1 to 2 kg/cm$^2$, and with a space velocity GHSV, evaluated on the stream of gas paraffins fed to the reactor, comprised within the range of from 100 to 10000 h$^{-1}$.

Some examples are now given to better illustrate the invention. It should be anyway understood that the invention is not limited to said examples, or by them.

EXAMPLE 1

A sample of titanium-silicalite with a granulometry smaller than 30 $\mu$m, prepared according to the process described in Example 1 of U.K. Pat. No. 2,071,071 is impregnated with a solution acidified by means of HCl, containing hexachloroplatinic acid and stannous chloride dihydrate, by using the following procedure:

1.16 g of $SnCl_2.2H_2O$ is dissolved in 8.6 cc of concentrated hydrochloric acid and the resulting solution is added to 4.07 g (2.5 cc) of an aqueous solution of hexachloroplatinic acid (containing 25% by weight of Pt).

The volume of the solution is adjusted to a total value of 60 cc with water, and the resulting solution is slowly added to 100 g of titanium silicalite.

When impregnation is complete, the resulting material is concentrated to dryness at a temperature of round 120° C., over a time of approximately 4 hours.

The dried material is calcined in a stream of air flowing at a GHSV of 500 h$^{-1}$, over a time of about 2 hours.

The calcined product is subsequently reduced in a stream of $H_2/N_2$ (molar ratio 1), at the temperature of 600° C. and flowing at a GHSV of 500 h$^{-1}$, over a time of about 2 hours.

A catalyst is eventually obtained, which has the chemical composition: 1% by weight of Pt, 0.6% by weight of Sn, 0.02% by weight of Cl−, 98.38% by weight of titanium-silicalite (2% by weight of Ti).

The catalyst is tested in the dehydrogenation of propane is a fluidized-bed reactor by operating at the temperature of 590° C., under a pressure of 1 kg/cm$^2$ and with a space velocity GHSV of 400 h$^{-1}$ referred to a catalyst bed obtained by diluting the catalyst in $\alpha$-alumina with a ratio of catalyst to $\alpha$-alumina of 0.06 by weight.

The results obtained are reported in Tables 1 and 2.

EXAMPLE 2

COMPARATIVE EXAMPLE

A sample of 100 g of silicalite, with a granulometry smaller than 30 $\mu$m, with the average size of the crystals being comprised within the range of from 20 to 26 $\mu$m, is impregnated with $SnCl_2.2H_2O$ and hexachloroplatinic acid, in solution acidified with hydrochloric acid, with such amounts being used, as to obtain an end catalyst having the following chemical composition: 1% by weight of Pt, 0.6% by weight of Sn, 0.01% by weight of Cl−, 98,39% by weight of silicalite.

The operating modalities of impregnation, drying, calcination and reduction are as disclosed in Example 1. The catalyst is eventually tested according to the procedure reported in Example 1, in the reaction of propane dehydrogenation.

The results obtained are shown in Table 1.

EXAMPLE 3

A sample of 100 g of microspheroidal alumina prepared according to the prior art with a granulometry smaller than 30 μm, a surface area of 250 m$^2$/g and a total porosity of 0.8 cc/g is impregnated with an alcoholic solution obtained by dissolving 7.2 of tetraethyl orthotitanate in 70 cc of ethyl alcohol, according to the following procedure.

100 g of alumina is charged to a quartz reactor installed inside a heating furnace.

From the bottom end of said quartz reactor, through the distributor, nitrogen is fed with such a flow rate as to have a linear speed inside the interior of the reactor, of about 2 cm/second, which causes the material to be fluidized. From the top end of the reactor an alcoholic solution of Ti(OC$_2$H$_5$)$_4$ — obtained by dissolving 7.2 g of tetraethyl orthotitanate in 70 cc of ethyl alcohol — is added dropwise, with the material being constantly kept at room temperature. When addition is complete, the heating of the material is started, and the material is gradually heated up to 550° C. When this temperature is reached, nitrogen flow is discontinued and the material is calcined in an air flow over 2 hours.

The product obtained after calcination at 550° C., containing 2.5% of TiO$_2$ by weight, is impregnated with a solution acidified with HCl, containing suitable amounts of SnCl$_2$.2H$_2$O and H$_2$PtCl$_6$, such as to obtain an end product containing; 1% by weight of Pt, 0.6% by weight of Sn, 2.45% weight of TiO$_2$, 0.02% by weight of Cl−, 95.93% by weight of Al$_2$O$_3$.

The operating modalities of impregnation and activation are the same as already cited in the preceding examples.

The catalyst was finally tested in the dehydrogenation of propane according to the modalities of Example 1. The results obtained are reported in Table 1.

EXAMPLE 4

COMPARATIVE EXAMPLE

A sample of microspheroidal alumina, prepared according to the prior art, with a granulometry smaller than 30 μm, a surface area of 250 m$^2$/g and a total porosity of 0.8 cc/g is impregnated with a solution acidified with hydrochloric acid, containing hexachloroplatinic acid and stannous chloride dihydrate, by the following procedure:

1.16 g of SnCl$_2$.2H$_2$O is dissolved in 8.6 cc of concentrated hydrochloric acid and the resulting solution is added to 4.07 g (2.5 cc) of an aqueous solution of hexachloroplatinic acid (at 25% by weight of Pt)

The volume of the solution is adjusted to a total value of 80 cc with water, and the resulting solution is slowly added to 100 g of alumina.

At the end of the impregnation, the material is concentrated to dryness, calcined and reduced under the same conditions as already described in Example 1.

A catalyst with the following chemical composition: 1% by weight of Pt, 0.6% by weight of Sn, 0.02% by weight of Cl−, 98.38% by weight of Al$_2$O$_3$ is obtained.

The catalyst is tested in the dehydrogenation of propane on a fluidized-bed catalyst, by following the procedure of Example 1.

The results are shown in Tables 1 and 2.

EXAMPLE 5

(COMPARATIVE EXAMPLE)

A sample of the same alumina used in Example 4 is admixed with silica by using esters of silicic acid, according to the following procedure.

100 g of alumina is charged to a quartz reactor installed inside a heating furnace.

From the bottom end of the quartz reactor, through the distributor, nitrogen is fed with such a flow rate as to have a linear speed inside the interior of the reactor, of about 2 cm/second, which causes the material to be fluidized. From the top an alcoholic solution of Si-(OC$_2$H$_5$)$_4$ — obtained by dissolving 34 g of tetraethyl orthosilicate in 43 cc of ethyl alcohol — is added dropwise, with the material being constantly kept at room temperature. When addition is complete, the heating of the material is started, and the material is gradually heated up to 550° C. When this temperature is reached, nitrogen flow is discontinued and the material is calcined in an air flow over 2 hours.

The resulting product has the following chemical composition: 11.5% by weight of SiO$_2$, 88.5% by weight of Al$_2$O$_3$, with a surface area of 245 m$^2$/g and a total porosity of 0.7 cc/g.

100 g of this material is impregnated with the same amounts as used in Example 1, of SnCl$_2$.2H$_2$O and hexachloroplatinic acid, by the same procedure as already known for catalyst preparation.

The catalyst is tested in the dehydrogenation of propane according to the modalities described in Example 1.

The results obtained are reported in table 1.

EXAMPLE 6

100 g of silica with a granulometry smaller than 30 μm, a surface area of 250 m$^2$/g and a total porosity of 0.6 cc/g is impregnated with an alcoholic solution obtained by dissolving 7.2 g of tetraethyl orthotitanate in 53 cc of ethyl alcohol, using the same procedure as described in Example 5. The product obtained after calcination at 550° C., containing 2.5% of TiO$_2$, is impregnated with a solution acidified with hydrochloric acid, and containing such suitable amounts of SnCl$_2$.2H$_2$O and H$_2$PtCl$_6$ as to obtain eventually a product containing 1% by weight of Pt, 0.6% by weight of Sn, 2.45% by weight of TiO$_2$ and 95.93% by weight of Al$_2$O$_3$ and 0.01% by weight of Cl−.

The modalities followed for the impregnation and the activation are the same as already cited in the preceding examples.

The catalyst is eventually tested in propane dehydrogenation, according to the modalities set forth in Example 1.

The results obtained are reported in Table 1.

EXAMPLE 7

COMPARATIVE EXAMPLE 100 g of silica with a granulometry smaller than 30 μm, a surface area of 250 m$^2$/g and a total porosity of 0.6 cc/g is impregnated with an aqueous solution acidified with hydrochloric acid, containing $SnCl_2 \cdot 2H_2O$ and hexachloroplatinic acid (same amounts as of Example 1), then impregnated silica is dried, calcined and reduced by following the same procedure also as described in Example 1.

At the end a catalyst is obtained, having the following chemical composition: 1% by weight Pt, 0.6% by weight Sn, 0.02% by weight Cl—, 98.38% by weight $SiO_2$, a surface area of 245 $m^2/g$, and a total porosity of 0.55 cc/g.

The catalyst was finally tested in propane dehydrogenation, under the same conditions as described in Example 1.

The results obtained are shown in Table 1.

TABLE 1

| Catalyst of Example No. | Conversion % | Selectivity % (by weight) | Yield % (by weight) | Pt %, referred to catalyst bed |
|---|---|---|---|---|
| 1 | 40 | 90 | 36 | 0.06 |
| 2 | 46 | 76 | 35 | 0.06 |
| 3 | 37 | 87 | 32 | 0.06 |
| 4 | 18 | 84 | 15 | 0.06 |
| 5 | 34 | 85 | 29 | 0.06 |
| 6 | 39 | 88 | 34 | 0.06 |
| 7 | 38 | 84 | 33 | 0.06 |

TABLE 2

Reactor Effluent T = 590° C.
GHSV = 400 $h^{-1}$
Catalyst diluted in α-alumina, ratio of catalyst to α-alumina 0.06 by weight

| | 1% Pt + 0.6% of Sn/$Al_2O_3$ Mol % | 1% Pt + 0.6% of Sn/titanium-silicalite Mol % |
|---|---|---|
| $H_2$ | 13.98 | 29.41 |
| $CH_4$ | 0.52 | 0.99 |
| CO | 0.12 | 0.08 |
| $CO_2$ | none | none |
| $C_2H_6$ | 0.15 | 0.68 |
| $C_2H_4$ | 0.36 | 0.15 |
| $C_3H_8$ | 70.06 | 41.58 |
| $C_3H_6$ | 12.47 | 25.58 |
| iso-$C_4H_{10}$ | 0.12 | 0.02 |
| n-$C_4H_{10}$ | none | none |
| $\Sigma C_4-$ | 0.21 | 0.07 |
| Coke | 1.99 | 1.62 |
| Heavy | 0.02 | 0.02 |

We claim:

1. A catalytic composition for the dehydrogenation of $C_2$–$C_5$-paraffins comprising:
   (a) platinum, in an amount within the range of from 0.01 to 3% by weight,
   (b) tin, in an amount within the range of from 0.06 to 1.5% by weight, and
   (c) a support comprising at least one selected from the group consisting of titanated silica and titanium silicalite, in which the amount of titanium in the support is within the range of from 0.05 to 3% by weight.

2. The catalytic composition according to claim 1, in which the support is titanated silica.

3. The catalytic composition according to claim 1, in which the support is titanium silicalite.

4. The catalytic composition according to claim 1, in which the amount of titanium in the support is within the range of from 1 to 2% by weight.

* * * * *